United States Patent [19]
Griffin, III

[11] Patent Number: 5,697,965
[45] Date of Patent: Dec. 16, 1997

[54] METHOD OF MAKING AN ATRIAL DEFIBRILLATION CATHETER

[75] Inventor: Joseph C. Griffin, III, Atco, N.J.

[73] Assignee: ProCath Corporation, Berlin, N.J.

[21] Appl. No.: 625,872

[22] Filed: Apr. 1, 1996

[51] Int. Cl.⁶ ............................................. A61N 1/05
[52] U.S. Cl. ............................................... 607/123
[58] Field of Search ........................ 607/122, 123, 607/4, 5

[56] References Cited

U.S. PATENT DOCUMENTS

| | | | |
|---|---|---|---|
| 3,448,739 | 6/1969 | Stark et al. . | |
| 3,634,924 | 1/1972 | Blake et al. . | |
| 3,746,003 | 7/1973 | Blake et al. . | |
| 3,833,004 | 9/1974 | Vazquez et al. . | |
| 3,995,623 | 12/1976 | Blake et al. . | |
| 4,328,806 | 5/1982 | Cooper . | |
| 4,329,993 | 5/1982 | Lieber et al. . | |
| 4,329,994 | 5/1982 | Cooper . | |
| 4,519,403 | 5/1985 | Dickhudt | 128/785 |
| 4,608,986 | 9/1986 | Beranek et al. | 607/123 |
| 4,898,176 | 2/1990 | Petre | 128/642 |
| 5,000,190 | 3/1991 | Petre . | |
| 5,140,987 | 8/1992 | Schuger et al. | 128/642 |
| 5,195,942 | 3/1993 | Weil et al. | 600/18 |
| 5,255,678 | 10/1993 | Deslauriers et al. | 128/642 |
| 5,304,139 | 4/1994 | Adams et al. . | |
| 5,403,351 | 4/1995 | Saksena . | |
| 5,411,475 | 5/1995 | Atala et al. | 604/54 |
| 5,433,729 | 7/1995 | Adams et al. . | |
| 5,441,483 | 8/1995 | Avitall | 604/95 |
| 5,571,159 | 11/1996 | Alt | 607/122 |

*Primary Examiner*—Scott Getzow
*Attorney, Agent, or Firm*—Wigman, Cohen, Leitner & Myers, P.C.

[57] ABSTRACT

A catheter for facilitating intracardiac atrial defibrillation includes an elongated flexible member that has a proximal end and a distal end. The flexible member further has a plurality of lumens that extend from the proximal end to the distal end thereof. An opening is formed through the flexible member adjacent the distal end thereof. One of the lumens communicates with the opening. A balloon envelope is secured to the periphery of flexible member and surrounds the opening. Connected to one end of the lumen associated with the opening is an air inlet tube. A syringe is provided to supply air through the inlet tube, through the lumen and out the opening in order to inflate the balloon envelope. A plurality of spaced apart electrode bands are secured around the periphery of the flexible member in a predetermined pattern. A plurality of electrical leads extend through the proximal end of the flexible member and through corresponding lumens to supply electrical current to the electrode bands.

10 Claims, 2 Drawing Sheets

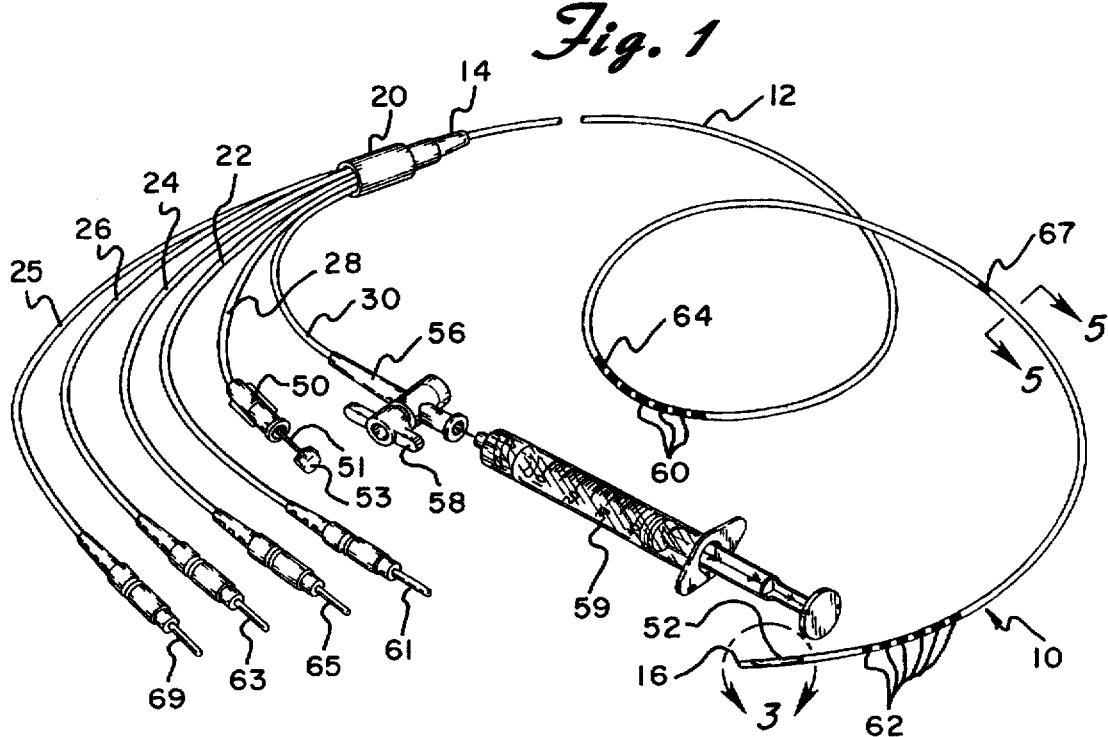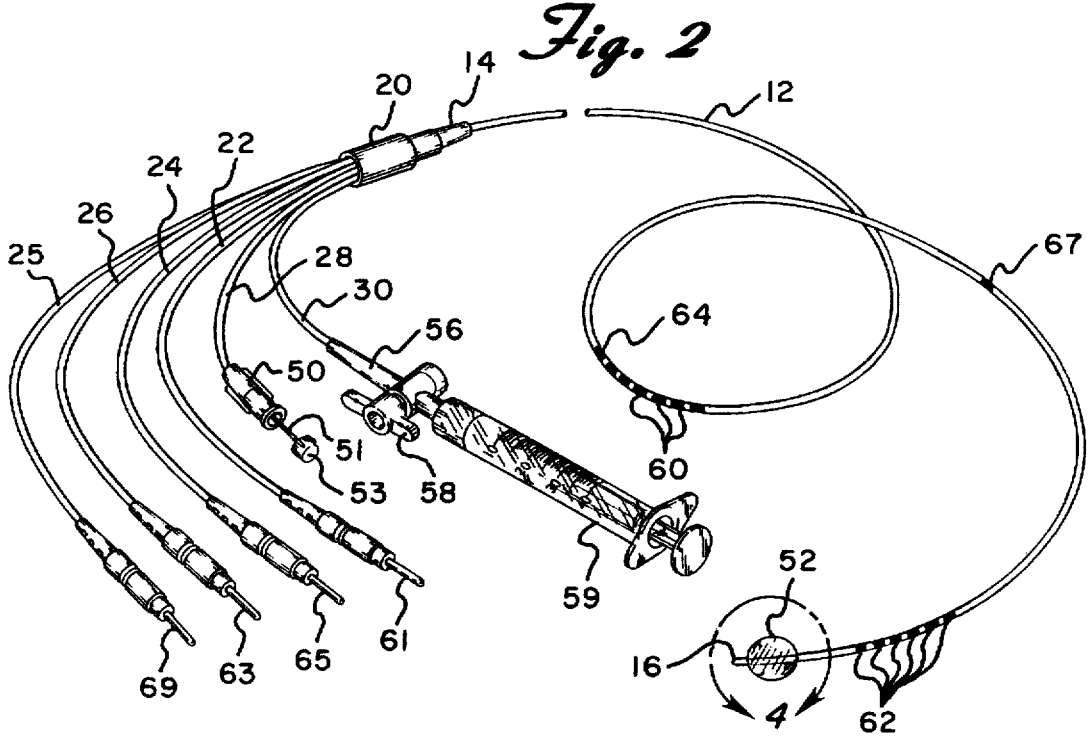

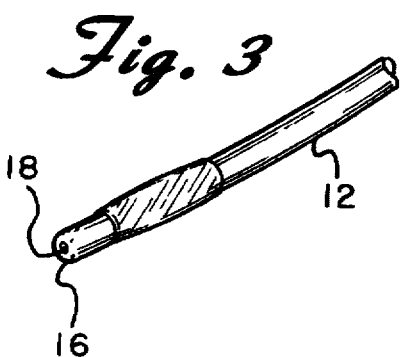
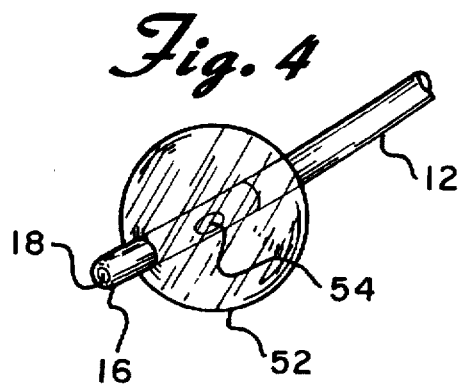
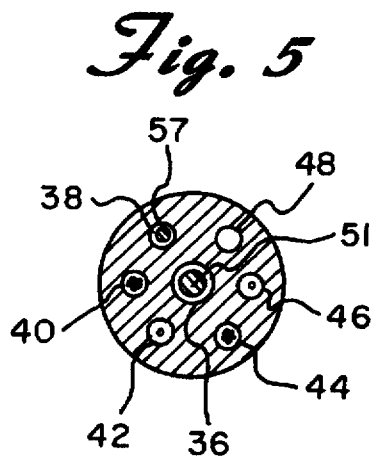
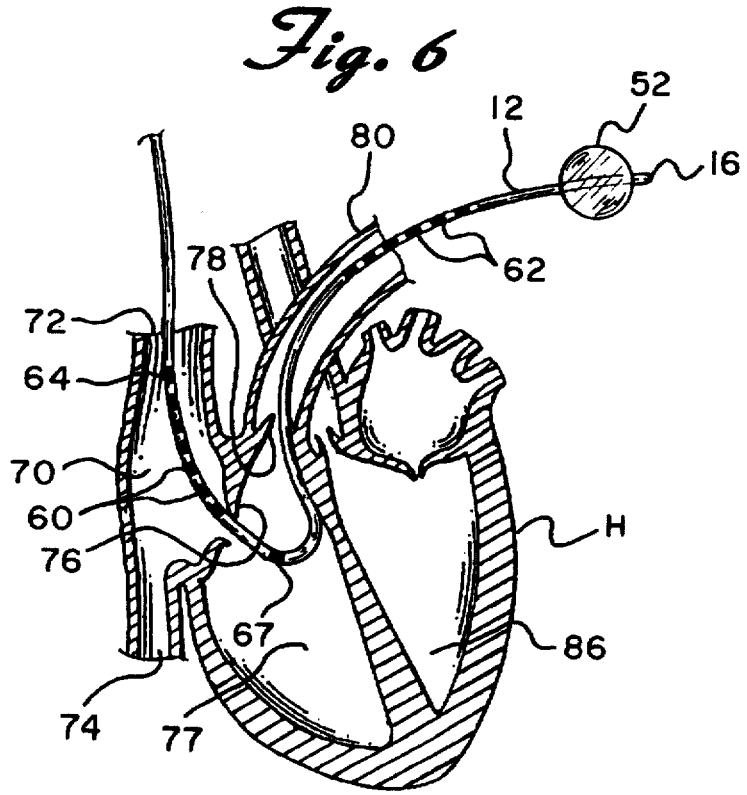

METHOD OF MAKING AN ATRIAL DEFIBRILLATION CATHETER

BACKGROUND OF THE INVENTION

The present invention relates generally to balloon catheters and, more particularly, toward a method and apparatus for facilitating intracardiac atrial defibrillation.

Atrial fibrillation is a common arrhythmia that afflicts more than 1.5 million patients in the U.S. alone. It is by far the most prevalent cardiac rhythm disorder associated with hospitalization. Symptoms associated with chronic atrial fibrillation include: awareness of irregularity, palpitations, fatigue and diminished exercise tolerance. Atrial fibrillation has also been recognized as one of the main contributing factors of embolic strokes.

The risks and symptoms associated with atrial fibrillation confirm the necessity for restoration of sinus rhythm. Two commonly employed methods for performing an intracardiac atrial defibrillation procedure are drug therapy and external cardioversion. With regard to drug therapy, studies have shown that there is a risk for proarrhythmic effects, especially in patients with atrial fibrillation and a history of congestive heart failure, which may outweigh the potential benefit of restoring sinus rhythm.

There are also risks associated with external cardioversion. Such risks result from the fact that high energy shocks (50 to 360 joules) are used during the procedure. The high energy shocks can cause heavy muscular contractions with a potential risk of spine or bone fractures, potential pronounced increase in muscle enzymes, induction of ventricular arrhythmias and overall negative influence on myocardial function. Further, the high energy shocks require the administration of a general anesthetic.

In recognition of the foregoing, a relatively new method has been developed. This method involves internal cardioversion using percutaneous transvenous catheter electrodes. Internal cardioversion can be performed with energies of less than 12 joules. However, existing multi-electrode catheters utilized in internal cardioversions cannot be sufficiently anchored in the pulmonary artery before the electro-shocks are administered. Further, such catheters typically do not have the proper arrangement of electrodes to provide the necessary electro-shocks to the appropriate locations.

SUMMARY OF THE INVENTION

The present invention is designed to overcome the deficiencies of the prior art discussed above. It is an object of the invention to provide a catheter for facilitating atrial defibrillation that can be readily anchored in the left pulmonary artery.

It is a further object of the invention to provide a method of performing an intracardiac atrial defibrillation.

In accordance with the illustrative embodiments, demonstrating features and advantages of the present invention, there is provided a catheter for facilitating intracardiac atrial defibrillation that includes an elongated flexible member that has a proximal end and a distal end. The flexible member further encompasses a plurality of lumens that extend from the proximal end to the distal end thereof. An opening is formed through the flexible member adjacent the distal end thereof. One of the lumens is adapted to communicate with the opening. A balloon envelope is secured to the periphery of flexible member and encompasses the opening. Connected to one end of the lumen associated with the opening is an air inlet tube. A syringe is provided to supply air through the inlet tube, through the lumen and out the opening in order to inflate the balloon envelope. A plurality of spaced apart electrode bands are secured around the periphery of the flexible member in a predetermined pattern. A plurality of electrical leads extend through the proximal end of the flexible member and through corresponding lumens to supply electrical current to the electrode bands.

Other objects, features and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a perspective view of the present invention showing the balloon envelope of the catheter deflated;

FIG. 2 is a view similar to FIG. 1 showing the balloon envelope inflated;

FIG. 3 is an enlarged view taken along line 3 of FIG. 1;

FIG. 4 is an enlarged view taken along line 4 of FIG. 2;

FIG. 5 is an enlarged cross-sectional view taken along lines 5—5 of FIG. 1, and

FIG. 6 is a partial plan view showing the catheter of the present invention inserted into a heart.

DETAILED DESCRIPTION OF THE PREFERRED EMBODIMENT

Referring now to the drawings in detail wherein like reference numerals have been used throughout the various figures to designate like elements, there is shown in FIG. 1 a catheter for facilitating atrial defibrillation constructed in accordance with the principles of the present invention and designated generally as 10. The catheter 10 is adapted to be positioned in a heart H as illustrated in FIG. 6.

The catheter 10 comprises an elongated flexible member 12 which is preferably made of polyurethane. However, the flexible member can be comprised of a variety of other plastic materials such as silicone rubber and plasticized PVC. The flexible member 12 is preferably 110 cm long (±5 cm) and has an outer diameter of approximately 2.5 mm.

Member 12 has a proximal end 14 and a distal end 16. The distal end has an outlet port 18 formed therethrough as illustrated in FIGS. 3 and 4. A manifold 20 is secured around the proximal end 14. Extending outwardly from the manifold 20 is a proximal electrical lead 22, an atrial pacing/sensing electrical lead 24, a ventricular pacing/sensing electrical lead 25, a distal electrical lead 26, a guide wire tube 28 and air inlet tube 30.

A central lumen 36 is formed through the center of the flexible member 12. The central lumen preferably has a diameter of approximately 0.7 mm. A plurality of lumens 38, 40, 42, 44, 46 and 48, also formed through the flexible member 12, circumscribe the central lumen 36. Each of the plurality of lumens has a somewhat smaller diameter than the central lumen.

The end of the guide wire tube 28 located within the manifold 20 is connected to the central lumen 36. Such connection allows for the passage of a guide wire (not shown). The guide wire facilitates the insertion of the catheter 10 into the patient. The guide wire tube 28 preferably terminates with a female connecting terminal 50, commonly referred to as a luer-lock hub extension. It should be noted that the central lumen 36 can be used for blood sampling, drug infusion and/or pressure measurement.

A removable, user formable stylet 51 can also be inserted into the guide wire tube 28 and the lumen 36 attached thereto. The stylet 51 preferably has a gripping member 53 secured to one end thereof and is comprised of TEFLON® coated steel. The stylet 51 is used to facilitate the steering of the distal end 16 of the catheter 10 in the left pulmonary artery as more fully described below.

The air inlet tube 30 communicates with lumen 48 which terminates distally under an inflatable balloon envelope 52. The balloon envelope is preferably made of latex and is 10 mm in length (FIGS. 3 and 4). The balloon envelope is secured around a portion of the periphery of the flexible member 12 adjacent the distal end 16 thereof. The balloon envelope 52 completely surrounds a lateral opening 54 formed through the flexible member 12. Lumen 48 is connected to the opening 54. Secured to the proximal end of the air inlet tube is a female connecting terminal 56 and an attached two-way stop cock 58. A syringe 59 is adapted to engage the connecting terminal 56 to supply air through the air inlet tube 30, the lumen 48 and out the opening 54 in order to inflate the balloon envelope 52. When the balloon envelope is inflated it preferably has a diameter of approximately 8 mm.

Lumen 38 is adapted to house a stiffening wire 57 (FIG. 3). The stiffening wire is preferably comprised of stainless steel and provides for increased control of the portion of the catheter which is positioned in the vena cava as more fully described infra. The stiffening wire preferably has one end anchored to the manifold 20 adjacent the proximal end 14 of the flexible member 12. The other end of the stiffening wire is preferably tapered and terminates approximately 10 cm from the distal end 16 of the flexible member 12. The end of the stiffening wire is tapered to prevent undesired bending near the proximal end 16 caused by an abrupt change in stiffness.

The proximal electrical lead 22 includes low resistance conductive wires which extend through lumen 40 and are connected in series to an array of six 5 mm electrode bands 60 which are spaced 5 mm apart. It should be noted that the spacing and number of electrode bands can be readily changed. In the preferred embodiment, the first electrode band in the array is located approximately 33 cm from the distal end 16 of the flexible member 12. The end of the electrical lead 22 which extends outwardly from the manifold 20 terminates in a contact pin 61.

The distal electrical lead 26 includes low resistance conductive wires which extend through lumen 44 and are connected in series to an array of six 5 mm electrode bands 62 which are spaced 4 mm apart. The first electrode band in this array is preferably located approximately 9 cm from the distal end 16 of the flexible member 12. The end of the electrical lead 26 which extends outwardly from the manifold 20 terminates in a contact pin 63.

The atrial pacing/sensing electrical lead 24 includes a low resistance conductor wire that extends through lumen 42 and is connected to a 5 mm electrode band (atrial pacing ring) 64. The electrode band 64 is located 34 cm from the distal end 16 of the flexible member 12. The end of the electrical lead 24 which extends outwardly from the manifold 20 terminates in a contact pin 65.

The ventricular pacing/sensing electrical lead 25 includes a low resistance conductor wire that extends through lumen 46 and is connected to a 5 mm electrode band 67 (ventricular pacing ring). The electrode band 67 is preferably located approximately 19 cm from the distal end 16 of the flexible member 12. The end of the electrical lead 25 which extends outwardly from the manifold 20 terminates in a contact pin 69.

To facilitate an understanding of the principles of the foregoing apparatus, its operation will now be briefly described. In order to perform a defibrillation procedure, the catheter 10 is introduced into the vascular system from the antecubital, femoral, subclavian, or jugular areas in a manner known in the art. The catheter is then guided into the patient's heart H until it is placed in the desirable position as shown in FIG. 6. If difficulties in maneuvering or advancing the catheter through the vascular system occur, a guide wire (not shown) can be inserted into the guide wire tube 28. The guide wire tube is connected to the lumen 36 and the insertion of the guide wire into the same increases the maneuverability of the catheter. Once the catheter has been advanced through the vascular system, the guide wire is removed from the tube 28.

The flexible member 12 of the catheter 10 is positioned so that the balloon envelope is positioned in the left pulmonary artery 80. Specifically, the distal end 16 of the catheter is passed through the superior vena cava vein 72, through the right atrium 70, through the tricuspid valve 76, up through the right ventricle, through the pulmonary valve 78 and into the left pulmonary artery 80. The stiffening wire can be used to provide better control of the passive portion of the catheter 10 (i.e., the portion of the catheter adjacent the distal end 16) when the same is passed through the superior vena cava 72.

The stylet 51, which extends from the female connecting terminal 50, is moved further into the flexible member 12 so that an end of the same is moved closer to the distal end 16 in order to facilitate the passing of the catheter through the tricuspid valve 76. This is accomplished by maneuvering gripping member 53 closer to the female connecting terminal 50. Once the distal end 16 has passed through the tricuspid valve, the stylet is moved away from the distal end 16 of the flexible member 12. The balloon envelope 52 can be inflated to float the tip of the catheter up through the pulmonary valve 78 and into the left pulmonary artery 80. The stylet 51 can be reinserted into the distal end 16 of the flexible member 12 and rotated in order to properly position the catheter in the left pulmonary arch (not shown). The physician rotates the stylet by rotating the attached gripping member (orbit knob) 53.

The catheter is positioned so that the electrode band 64 is positioned in the right atrium 70, the electrode band 67 is situated in the right ventricle 77, the electrode bands 60 are situated in the right atrium 70 and the electrode bands 62 are situated in the left pulmonary artery 80.

When the catheter 10 is so situated, the balloon envelope 52 is inflated. This is accomplished by opening stop cock 58 and depressing the plunger portion of the syringe 50 so that air is forced through the air inlet tube 30, through the lumen 48 associated therewith and out the opening 54. The inflating of the balloon envelope ensures that the catheter 10 is properly anchored in the pulmonary artery 80.

With the catheter properly in place, electric shocks are applied through the same in order to defibrillate the patient's heart H. This is accomplished by connecting the contact pins 61, 63, 65 and 69 to an appropriate power source. Thereafter, electrical current is supplied through the electrical leads 22, 24 25 and 26 to the corresponding electrode bands 60, 64, 67 and 62 in order to achieve a normal sinus rhythm in the patient. More specifically, electrode band 64, which is connected to atrial pacing/sensing lead 24, and electrode band 67, which is connected to ventricular pacing/sensing lead 25, sense the occurrence, if any, of fibrillation. If fibrillation is sensed, the heart is defibrillated or cardioverted by the application of at least one electrical shock between the array of the electrode bands 60 and the array of electrode bands 62 which are connected to the proximal and distal electrical leads 22 and 26, respectively.

The present invention may be embodied in other forms without departing from the spirit or essential attributes thereof and accordingly reference should be made to the claims rather than to the foregoing specification as indicating the scope thereof.

What is claimed is:

1. A method for manufacturing a catheter adapted for temporary placement in the body of a patient to treat atrial fibrillation, comprising the steps of:

fabricating a small diameter, elongated, flexible member having a proximal end, a distal end, and a central portion between said proximal end and said distal end, wherein said member has a diameter, length, and flexibility adapted to permit it to be introduced into the patient's vascular system and maneuvered so that its distal end may be advanced along a path including the right atrium, tricuspid valve, right ventricle, pulmonary valve, and into a predetermined position in the left pulmonary artery adjacent the left atrium of the patient's heart;

forming a plurality of lumens in said member, each extending from a respective port at the proximal end and through at least a portion of the length of said member including the central portion thereof and generally axially thereof;

connecting said lumens to a manifold attached at the proximal end of said member;

attaching a plurality of tubes to the proximal end of said manifold such that each tube is connected with a respective lumen;

forming adjacent the distal end of said member an opening into one of said plurality of lumens that terminates at a point short of said distal end;

sealing a balloon envelope to said member adjacent the distal end thereof to place said opening within the envelope, whereby the balloon envelope may be selectively inflated and exhausted from a port and tube at the proximal end of the member via the lumen connected to said opening, so that the balloon may be sufficiently inflated during advancement of said member along said path to aid in floating the distal end of said member into said predetermined position in the pulmonary artery, and fully inflated to anchor the distal end in said predetermined position;

forming one of said plurality of lumens to extend completely through said member from the respective port and tube at the proximal end to a port at the distal end thereof, and with a diameter suitable to accommodate a guide wire to facilitate maneuvering said member along said path, and, when the guide wire is not present after the distal end of said member is anchored in said predetermined position in the pulmonary artery by the inflated balloon, to enable blood sampling, drug infusion or pressure measurement at the distal end of the member via the port thereat;

providing first and second arrays of defibrillation electrodes on said member, each of said arrays including a plurality of axially substantially uniformly spaced-apart electrically conductive relatively low impedance bands circumferentially encircling a respective segment of and conforming in shape to said central portion to maintain a substantially smooth continuous surface therewith without adversely affecting the flexibility of said member, wherein the first electrode array is located relatively more proximally along said central portion and the second electrode array is located relatively more distally along said central portion, and said first and second electrode arrays are spaced apart by a predetermined distance between the respective bands closest to one another in the two arrays, said predetermined distance being selected to place said first electrode array in the right atrium and said second electrode array in the pulmonary artery adjacent the left atrium when the distal end of said member is in said predetermined position in the pulmonary artery, and wherein the plurality of bands of said first electrode array are electrically interconnected for energization from a single source of electrical power and the plurality of bands of said second electrode array are electrically interconnected for energization from a single source of electrical power located external to the patient's body;

running at least a first relatively low resistance lead electrically connected to a band of said first electrode array through a lumen in said member for exit through the respective lumen port and tube at the proximal end thereof, running at least a second relatively low resistance lead electrically connected to a band of said second electrode array through a lumen in said member for exit through the respective lumen port and tube at the proximal end thereof, and connecting said first and second exiting leads to respective first and second electrical connectors adapted to be connected to a power source for application of electrical defibrillating shocks across said first and second electrode arrays when said member is in said path with the distal end in said predetermined position and the patient's heart is detected to be in atrial fibrillation;

providing on the central portion of said member additional first and second electrodes comprising respective electrically conductive relatively low impedance bands circumferentially encircling a respective segment of and conforming in shape to said central portion to maintain a substantially smooth continuous surface therewith, wherein said additional first and second electrodes are positioned and axially spaced apart on said central portion such that when the member is in place along said path with its distal end in said predetermined position in the pulmonary artery the additional first electrode will be positioned in the right atrium and the additional second electrode will be positioned in the right ventricle of the patient's heart, for use in pacing and sensing intracardiac activity of the patient's heart; and running an additional first relatively low resistance lead electrically connected to the additional first electrode band through a lumen in said member for exit through the respective lumen port and tube at the proximal end thereof, running an additional second relatively low resistance lead electrically connected to the additional second electrode band through a lumen in said member for exit through the respective lumen port and tube at the proximal end thereof, and connecting the additional first and second exiting leads to respective first and second electrical connectors adapted to be connected to pacing and sensing circuitry located external to the patient's body.

2. The method of claim 1, including the step of fabricating said member from a biocompatible plastic material.

3. The method of claim 2 wherein said biocompatible plastic material is selected from the group consisting of polyurethane, silicone rubber, and plasticized PVC.

4. The method of claim 1, wherein the bands in said first and second defibrillation electrode arrays are each approximately 5 millimeters wide and spaced apart from their respective neighboring bands in the respective array by a distance of about 4 to 5 millimeters.

5. The method of claim 4, wherein said member has a length of approximately 110 centimeters, and an outer diameter of about 2.5 millimeters.

6. A method for manufacturing a catheter adapted for temporary placement in the body of a patient to treat atrial fibrillation, comprising the steps of:

fabricating a small diameter, elongated, flexible member having a proximal end, a distal end, and a central portion between said proximal end and said distal end, wherein said member has a diameter, length, and flexibility adapted to permit it to be introduced into the patient's vascular system and maneuvered so that its distal end may be advanced along a path including the right atrium, tricuspid valve, right ventricle, pulmonary valve, and into a predetermined position in the left pulmonary artery adjacent the left atrium of the patient's heart;

forming at least six lumens in said member, each extending from a respective port at the proximal end and through at least a portion of the length of said member including the central portion thereof and generally axially thereof, a first one of said lumens communicating with a balloon at the distal end of said member, a second one of said lumens being arranged along the longitudinal axis of said member and extending from end to end of the member with a port at the distal end and having a diameter suitable to accommodate a guide wire to facilitate maneuvering said member along said path, and, when the guide wire is not present after the distal end of said member is anchored in said predetermined position in the pulmonary artery by the inflated balloon, to enable blood sampling, drug infusion or pressure measurement at the distal end of the member via the port thereat, another four of said lumens accommodating electrical leads to enable defibrillation and pacing;

connecting said lumens to a manifold attached at the proximal end of said member; and attaching at least six tubes to the proximal end of said manifold such that each tube is connected with a respective one of said at least six lumens.

7. The method of claim 6, further including the steps of:

forming at least a seventh lumen in said member radially offset from the longitudinal axis and extending from a respective port at the proximal end and through at least a portion of the length of said member including the central portion and generally axially thereof;

inserting a stiffening wire in said seventh lumen; and anchoring said stiffening wire to said manifold.

8. The method of claim 6, further including the steps of:

forming adjacent the distal end of said member an opening into the first one of said at least six lumens that terminates at a point short of said distal end; and sealing a balloon envelope to said member adjacent the distal end thereof to place said opening within the envelope, whereby the balloon envelope may be selectively inflated and exhausted from a port and tube at the proximal end of the member via the lumen connected to said opening, so that the balloon may be sufficiently inflated during advancement of said member along said path to aid in floating the distal end of said member into said predetermined position in the pulmonary artery, and fully inflated to anchor the distal end in said predetermined position.

9. The method of claim 8, further including the steps of:

attaching a syringe and stopcock to the tube connected to the lumen in which said opening is formed for inflating and deflating said balloon envelope.

10. The method of claim 9, further including the steps of:

providing first and second arrays of defibrillation electrodes on said member, each of said arrays including a plurality of axially substantially uniformly spaced-apart electrically conductive relatively low impedance bands circumferentially encircling a respective segment of and conforming in shape to said central portion to maintain a substantially smooth continuous surface therewith without adversely affecting the flexibility of said member, wherein the first electrode array is located relatively more proximally along said central portion and the second electrode array is located relatively more distally along said central portion, and said first and second electrode arrays are spaced apart by a predetermined distance between the respective bands closest to one another in the two arrays, said predetermined distance being selected to place said first electrode array in the right atrium and said second electrode array in the pulmonary artery adjacent the left atrium when the distal end of said member is in said predetermined position in the pulmonary artery, and wherein the plurality of bands of said first electrode array are electrically interconnected for energization from a single source of electrical power and the plurality of bands of said second electrode array are electrically interconnected for energization from a single source of electrical power located external to the patient's body;

running first and second relatively low resistance leads electrically connected to a respective band of said first and second electrode array through a respective lumen in said member for exit through the respective lumen port and tube at the proximal end thereof;

connecting said first and second exiting leads to respective first and second electrical connectors adapted to be connected to a power source for application of electrical defibrillating shocks across said first and second electrode arrays when said member is in said path with the distal end in said predetermined position and the patient's heart is detected to be in atrial fibrillation;

providing on the central portion of said member third and fourth electrodes comprising respective electrically conductive relatively low impedance bands circumferentially encircling a respective segment of and conforming in shape to said central portion to maintain a substantially smooth continuous surface therewith, wherein said third and fourth electrodes are positioned and axially spaced apart on said central portion such that when the member is in place along said path with its distal end in said predetermined position in the pulmonary artery, the third electrode will be positioned in the right atrium and the fourth electrode will be positioned in the right ventricle of the patient's heart, for use in pacing and sensing intracardiac activity of the patient's heart; and running a third relatively low resistance lead electrically connected to the third electrode band through a lumen in said member for exit through the respective lumen port and tube at the proximal end thereof, running a fourth relatively low resistance lead electrically connected to the fourth electrode band through a lumen in said member for exit through the respective lumen port and tube at the proximal end thereof, and connecting the third and fourth exiting leads to respective third and fourth electrical connectors adapted to be connected to pacing and sensing circuitry located external to the patient's body.

* * * * *